United States Patent
Wong et al.

(10) Patent No.: US 12,279,912 B2
(45) Date of Patent: Apr. 22, 2025

(54) SPECTRAL DOPPLER ENVELOPE TRACING WITHOUT ALIAS IN MEDICAL ULTRASOUND

(71) Applicant: Siemens Medical Solutions USA, Inc., Malvern, PA (US)

(72) Inventors: King Wong, Issaquah, WA (US); Chengzong Han, Bellevue, WA (US); Paul Donald Freiburger, Seattle, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 393 days.

(21) Appl. No.: 18/062,154

(22) Filed: Dec. 6, 2022

(65) Prior Publication Data

US 2024/0180525 A1 Jun. 6, 2024

(51) Int. Cl.
*A61B 8/00* (2006.01)
*G01S 15/89* (2006.01)
*G01S 7/52* (2006.01)

(52) U.S. Cl.
CPC .......... *A61B 8/488* (2013.01); *G01S 15/8979* (2013.01); *G01S 7/52066* (2013.01)

(58) Field of Classification Search
CPC ......... A61B 8/52; A61B 8/461; A61B 8/5269; A61B 8/5207; G01S 7/5207; G01S 15/8979
See application file for complete search history.

(56) References Cited

U.S. PATENT DOCUMENTS

| 5,287,753 | A | 2/1994 | Routh et al. |
| 2010/0234731 | A1 | 9/2010 | Lu et al. |
| 2014/0018680 | A1* | 1/2014 | Guracar ............... A61B 8/5276 600/440 |
| 2018/0000456 | A1* | 1/2018 | Wong .................... A61B 8/488 |
| 2018/0344292 | A1 | 12/2018 | Viggen et al. |

FOREIGN PATENT DOCUMENTS

| EP | 1797455 B1 | 7/2009 |
| JP | 2008511367 A | 4/2008 |
| JP | 5566673 B2 | 6/2014 |

OTHER PUBLICATIONS

Tortoli, P. I. E. R. "A tracking FFT processor for pulsed Doppler analysis beyond the Nyquist limit (medical ultrasound)." IEEE transactions on biomedical engineering 36.2 (1989): 232-237.

\* cited by examiner

*Primary Examiner* — Boniface N Nganga (57) ABSTRACT

For spectral Doppler imaging, the search range for tracing the spectral envelope is set dynamically. The limit for searching for the envelope is established by spectrum-by-spectrum placement between bands. This search may be aided by plotting the spectra from 0 to $2\pi$. The limit varies over time to better separate bands so that subsequent tracing avoids aliasing.

20 Claims, 4 Drawing Sheets

SPECTRAL DOPPLER ENVELOPE TRACING WITHOUT ALIAS IN MEDICAL ULTRASOUND

BACKGROUND

The present embodiments relate to Doppler mode (e.g., spectral) imaging. By transmitting a plurality of pulses (e.g., pulsed wave (PW)) at a location, a Doppler response is generated. For spectral Doppler, the frequency spectrum of the object's motion or flow for a single spatial region is estimated and displayed as a function of time. Spectral Doppler ultrasound imaging provides an image of spectra as velocity values (vertical axis) modulated by energy as a function of time (horizontal axis) for a gate. The spectra may be used for studying fluid flow or tissue motion within a patient.

Spectral Doppler may suffer from aliasing. Envelopes may display incorrectly in the presence of spectral aliasing. In spectral envelope tracing where there is spectral aliasing, the trace will not follow the peak correctly. Instead, the trace is clipped at Nyquist, baseline, or anywhere in between depending on spectral bandwidth and signal-to-noise ratio (SNR). Although aliasing may sometimes be corrected with a baseline shift, correction is not always possible even though the sampling frequency is less than maximum Doppler shift. This is because the search range for tracing is typically fixed at a Nyquist limit determined by the baseline position.

SUMMARY

By way of introduction, the preferred embodiments described below include methods, systems, computer readable media, and instructions for spectral Doppler imaging. The search range for tracing the spectral envelope is set dynamically. The limit for searching for the envelope is established by spectrum-by-spectrum placement between bands. This search may be aided by plotting the spectra from 0 to $2\pi$. The limit varies over time to better separate bands so that subsequent tracing avoids aliasing.

In a first aspect, a method is provided for spectral Doppler imaging. An ultrasound system acquires samples representing response from a range gate. A Doppler estimator estimates spectra over time for the range gate from the samples. The spectra are plotted over time from 0 to $2\pi$. For each spectrum of the spectra, a point in a noise region is identified between a first signal and a second signal, 0, or $2\pi$. A spectral envelope is traced over time. The tracing is limited by the points for the spectra. The spectral envelope or information derived from the spectral envelope is displayed in an image.

In one embodiment, the samples are acquired by transmitting with a pulse repetition frequency and acquiring one of the samples in response to each repetition. In another embodiment, a Fourier transform is applied to the samples to estimate. Each spectrum of the spectra is energy as a function of frequency for a period.

According to an embodiment, plotting includes plotting each spectrum to begin at 0 and end at $2\pi$ such that negative signal extends from $2\pi$ towards 0 and positive signal extends from 0 towards $2\pi$.

In various embodiments, the point is identified by positioning the point halfway between the first signal and the second signal, 0, or $2\pi$; searching for a band with the first signal and a band with the second signal in the spectrum, and positioning the point in the noise region between the first signal and (1) the second signal when the second signal is found in the searching or (2) 0 or $2\pi$ when the second signal is not found; determining a noise level from at least some of the spectra and using the noise level to search for the first and second signals; and/or positioning a boundary over time, the boundary formed by the points of the spectra and varying relative to 0 and $2\pi$.

In another embodiment, tracing includes locating an edge of the first signal with the noise region and locating an edge of the second signal with the noise region, the locating the edges being over time, and the edges being the spectral envelope. In yet another embodiment, the tracing includes using 0 or $2\pi$ for the spectra where the noise region extends to 0 or $2\pi$ and the first or second signal where the noise region does not extend to 0 or $2\pi$. As another embodiment, tracing includes tracing the first signal as a positive signal as between 0 to the points for the spectra and tracing the second signal as a negative signal as between $2\pi$ and the points for the spectra.

According to an embodiment, displaying includes displaying the spectral envelope with positive above a baseline and negative below a baseline. As another embodiment, displaying includes displaying the information, the information being based on a peak velocity of the spectral envelope.

In a second aspect, a method is provided for spectral Doppler imaging. An ultrasound system acquires samples representing response from a range gate. A Doppler estimator estimates spectra over time for the range gate from the samples. The spectra are plotted over time from 0 to $2\pi$. The positive and/or negative spectral envelopes are detected over time based on the spectra as plotted from 0 to $2\pi$. The spectral envelope or information derived from the spectral envelope is displayed in an image.

In one embodiment, plotting includes plotting each spectrum to begin at 0 and end at $2\pi$ such that negative signal extends from $2\pi$ towards 0 and positive signal extends from 0 towards $2\pi$. In an embodiment, detecting includes setting a boundary that varies along the 0 to $2\pi$ spectrum by spectrum, and searching for the positive spectral envelope on one side of the boundary and searching for the negative spectral envelope on another side of the boundary. According to another embodiment, setting the boundary includes setting the boundary halfway between signals of different bands where 0 or $2\pi$ is used instead of the signal for spectrum without signal in the band.

In a third aspect, a system is provided for spectral Doppler imaging. A beamformer is configured to sample a gate at a pulse repetition interval established in response to a velocity scale. A Doppler estimator is configured to generate multiple spectra from the sampling of the gate. A signal processor is configured to identify a line in a noise region between two bands or one of the bands and 0 and $2\pi$, the line varying over time spectrum-by-spectrum of the spectra and limit a search for a spectral envelope of the spectra by the line. A display is configured to display the spectral envelope or information derived from the spectral envelope.

As one embodiment, the signal processor is configured to plot the spectra from 0 to $2\pi$ such that one of the two bands is by $2\pi$ and the other of the two bands is by 0 and identify the line from the spectra as plotted in a noise region. In yet another embodiment, the signal processor is configured to position the line spectrum-by-spectrum halfway between the two bands.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
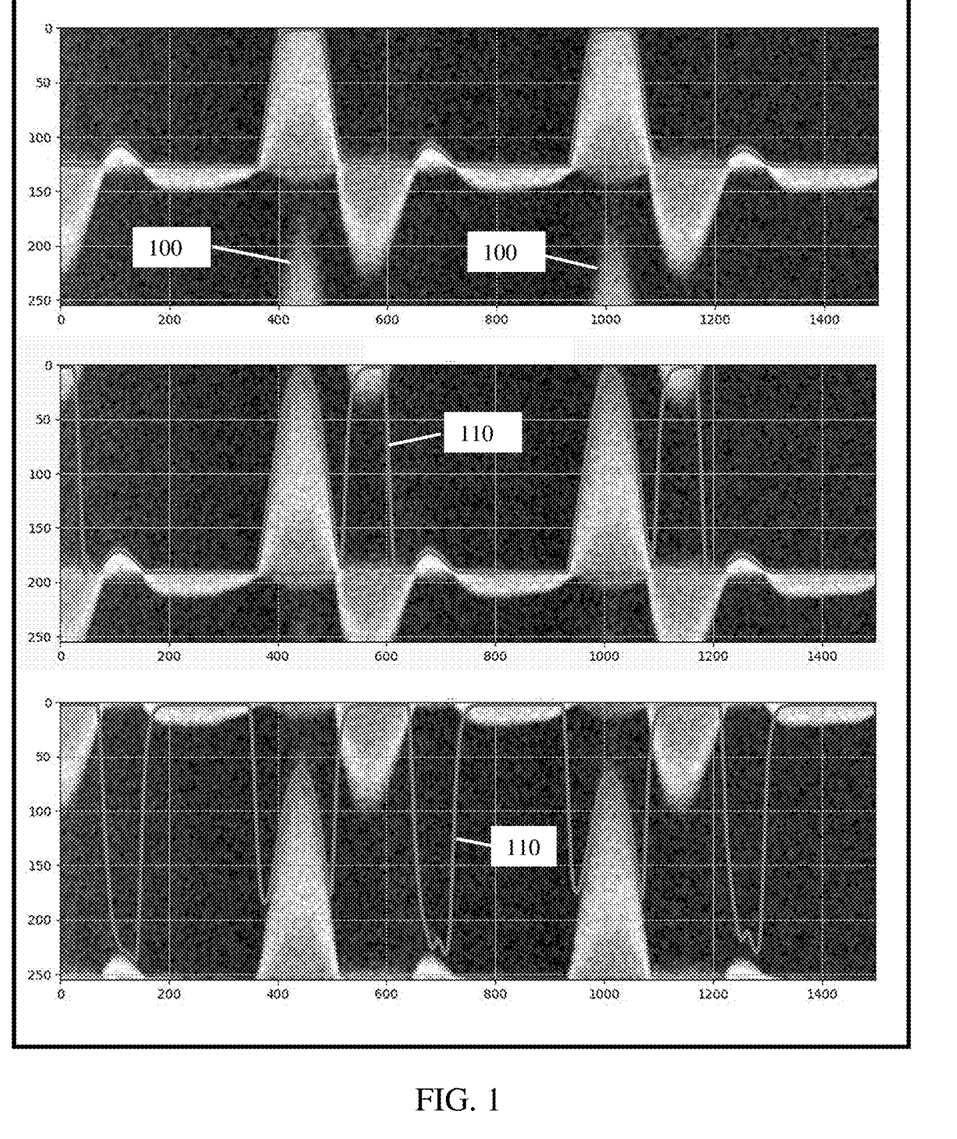
FIG. 1 illustrates aliasing in spectral Doppler imaging.

FIG. 1 shows three spectral Doppler images with different baseline settings. Each column in each image is represents a spectrum. The spectra over time are plotted in the velocity scale based on the Nyquist criterion given the sampling rate used to form the spectra. In the top spectral strip, the base line is set at 0 so the velocity scale range is from $-\pi$ to $\pi$. The result is aliasing 100 where some of the positive signal is placed at the negative portion of the strip (i.e., below the baseline). The middle strip shows shifting the baseline by $-0.25$ (25% shift negative). The result is aliasing of the negative signal into the positive region. When the trace 110 is detected, this negative signal is traced as a positive peak. The bottom strip shows further aliasing by further shifting the baseline to $-0.5$ (50% shift negative). Similarly, positive baseline shifts would result in greater aliasing of the positive signal into the negative.

The approach herein avoids aliasing. A spectral Doppler envelope is traced without aliasing even where baseline shift will not work. The search range for peak positive and negative flows are adjusted dynamically instead of fixed as set by the baseline position. The boundary between positive and negative flow is dynamically determined for each spectral column and then used as Nyquist limits for the subsequent positive search and negative search. The search limits are dynamically determined based on spectral characteristics such as bandwidth and signal-to-noise ratio (SNR). In this way, any existing peak search works correctly and produces an envelope consistent with the spectral contents. By adjusting the search range dynamically, the true peak velocities in either direction can be correctly detected even in the presence of spectral aliasing. Likewise, the envelope can be displayed correctly. Both positive and negative flow envelopes are correctly traced in the presence of spectral aliasing. The situation where the envelope gets confused due to aliasing of the Doppler signal itself is handled, improving the ability to extract diagnostically useful information as compared to envelope tracing using existing technology. When the maximum Doppler shift is less than the sampling rate, both the positive and negative envelopes are correctly displayed without aliasing artifacts.

Figure 2:
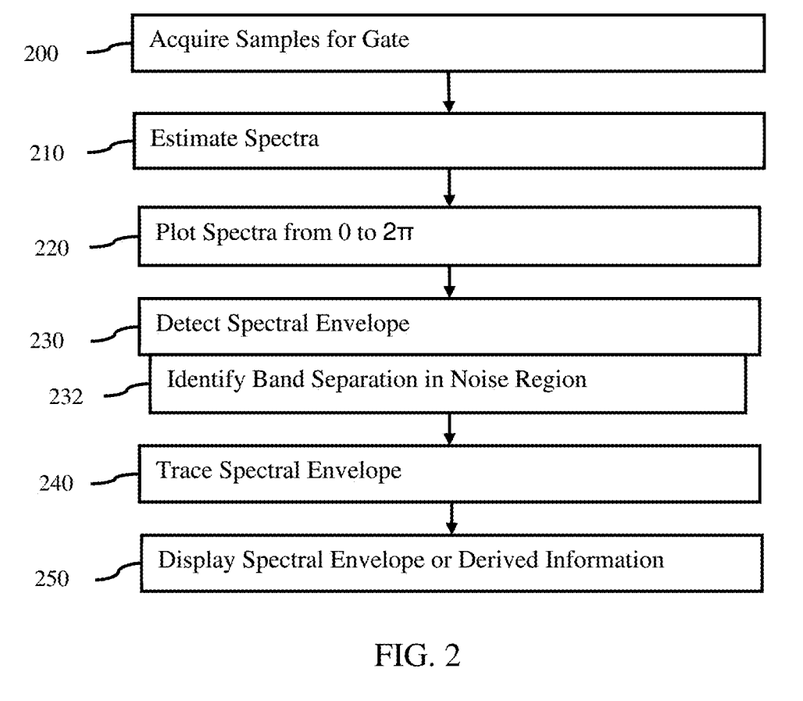
FIG. 2 is a flow chart diagram of one embodiment of a method for spectral Doppler imaging with an improved limit in tracing to avoid aliasing.

FIG. 2 shows one embodiment of a flow chart of a method for spectral Doppler imaging. By plotting the spectra in a way to distinguish positive and negative signal, a variable limit is identified between the two bands of the spectra. This limit is then used to trace the positive and/or negative signals, avoiding aliasing.

Figure 5:
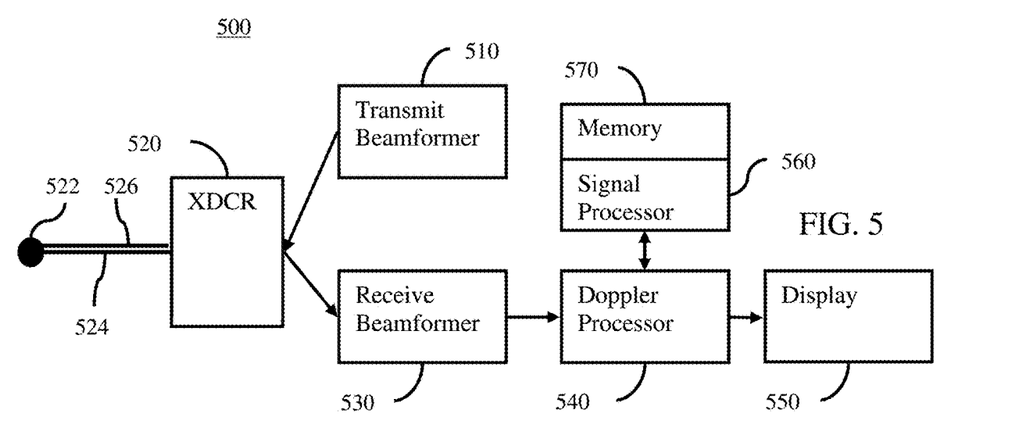
FIG. 5 is a block diagram of one embodiment of a system for spectral Doppler imaging with reduced aliasing.

The method is implemented by the system 500 of FIG. 5 or a different system. For example, an ultrasound system, such as a beamformer and transducer, or another ultrasound scanner acquires samples. A processor, such as a Doppler estimator, estimates spectra, plots, detects/identifies, and traces from the spectra. The ultrasound system or scanner displays an image of the traced spectral envelope or information from the spectral envelope. One or more acts may be performed through interaction with a user (e.g., gate placement for sampling). Other acts or all the acts may be performed automatically without user input other than initial activation or gate location determination.

The acts are performed in the order shown, but other orders are possible. Additional, different, or fewer acts may be provided. For example, act 250 is not performed. As another example, act 230 and/or 232 is not performed. In another example, act 220 is not performed. In yet another example, acts for gate placement, gate sizing, velocity scale setting, pulse repetition frequency setting, filtering, processing, maximum velocity determination over time, or other Doppler functions are provided.

The method is implemented for pulsed wave (PW) spectral Doppler. In PW, a gate location is sampled using pulsed wave transmissions (e.g., each pulse using a waveform of 1-50 cycles) interleaved with echo reception. PW may interleave with other modes of imaging, such as B-mode or flow-mode. Alternatively, continuous wave Doppler is used. With continuous wave Doppler, samples are created, which samples may be transformed to create spectra.

For spectral Doppler imaging, the sample gate, range gate, or spectral Doppler gate is positioned. For example, a B-mode and/or flow-mode scan is performed. The user indicates a gate location on the resulting image. In other examples, the gate is automatically positioned, such as at a location of greatest Doppler velocity or energy determined from flow-mode data. The user or automated process also determines the size of the gate, such as a depth or length in range. The lateral extent and/or range extent may be a default, based on data, user set, or otherwise selected.

In act 200, the ultrasound system acquires samples representing the range gate location. The samples are beamformed samples, but may be other raw data (e.g., channel data). In alternative embodiments, the samples are acquired by loading from memory or transfer from another device.

For acquisition by scanning, a transducer transmits a plurality of beams of acoustic energy in a sequence. The acoustic or ultrasound energy of each transmission is focused at or near the gate. A sequence of transmissions is performed. The repetition allows reception of sufficient samples to perform spectral or other Doppler analysis. Any ensemble number, such as 3-512, of transmit beams are transmitted so that a spectrum of the response from the Doppler gate may be estimated.

By performing additional transmissions, additional information is obtained for estimating spectra at other times or periods. A given response to a given beam may be used for different spectra (i.e., different times), such as where a moving window of received responses or samples is used to generate each spectrum.

A sufficient number of samples are acquired for a velocity scale set for the spectral Doppler imaging. The ultrasound system uses the velocity scale for the imaging. The velocity scale defines a range of frequencies over which the spectra or velocity is estimated and displayed. The velocity scale is selected by the user, a default or predetermined value of the system, and/or is adaptively determined by the ultrasound system. Based on the velocity scale, the transmissions are performed at a pulse repetition frequency or interval sampling the motion or flow signal at the gate location.

In response to the transmissions, the transducer receives acoustic echoes. A receive beamformer samples the echoes to acquire received signals for the gate. Receive beams are formed by focusing the received signals to coherently combine data representing the gate. This combined data representing the gate are beamformed signals or samples.

The receive operation occurs repetitively in response to the repetitive transmissions. Beamformed samples from the gate location at different times are received. A sample is received in response to each transmission. Samples for the same location are acquired over time in an ensemble. For Doppler analysis, an ensemble of samples from a same location is acquired. The samples may be obtained in an ongoing manner such that a moving window (e.g., ensemble or flow sample count) with any step size (e.g., every sample or every third sample) used to estimate a spectrum.

In act 210, a Doppler estimator estimates a spectrum for the Doppler gate from the samples of an ensemble or flow sample count. By repeating for other ensembles or flow sample counts, multiple spectra are estimated for a corresponding multiple times or periods (i.e., over time).

Each spectrum represents the energy as a function of frequency or velocity for a same period. Frequency has a known relationship to velocity, so expression in terms of frequency provides velocity and expression in terms of velocity provides frequency.

The spectra are estimated by applying a Fourier transform, wavelet transform, or Wigner-Ville distribution to the sequence of ultrasound responses or samples. Any transform may be applied to determine each spectrum.

The spectra are estimated using the velocity scale. The signal from the fluid or tissue is over a range of positive and negative velocities. The range used in the estimation is the velocity scale. Any velocities beyond the velocity scale wrap around or are aliased. The spectra provide energy as a function of frequency over the range of frequencies set by the velocity scale. The baseline determines the band ranges within the velocity scale.

Spectra are estimated for the Doppler gate. The spectra are estimated from the ultrasound samples in the sequence of samples from the Doppler gate. Each spectrum corresponds to a period in which the samples were acquired.

Acts 200 and 210 are repeated for different times or periods. To create a spectral strip, a spectrum for each of different times is determined. The spectrum for a given time (period) in a spectral strip is mapped with velocity on the vertical axis and energy modulating the intensity. The spectra are distributed in time along the horizontal axis. Other mapping may be used.

By repeating the acts, the spectra for the different times are acquired. As further samples are acquired, the further samples are added to the group and old samples removed. A sequence of spectra represents the Doppler gate at different times. Other spectra may be estimated for other periods or different times corresponding to different periods or ensembles of acquisition. The periods may overlap, such as when using a moving window with a step size less than the ensemble period or may be unique. The acquisition of samples and estimating for a different period are repeated to provide spectra over time. For a spectral strip, the process and corresponding repetition is on-going or occurs multiple times.

In act 220, a signal processor plots the spectra over time from 0 to $2\pi$. Rather than using $-\pi$ to $\pi$ with baseline 0 or other shift less than 100% (e.g., 25% or −50%) in the baseline (e.g., $-0.75\pi$ to $1.25\pi$), the spectra are plotted from 0 to $2\pi$. The spectra may be substantially plotted from 0 to $2\pi$, where substantially accounts for a 10% shift or less.

Figure 3:
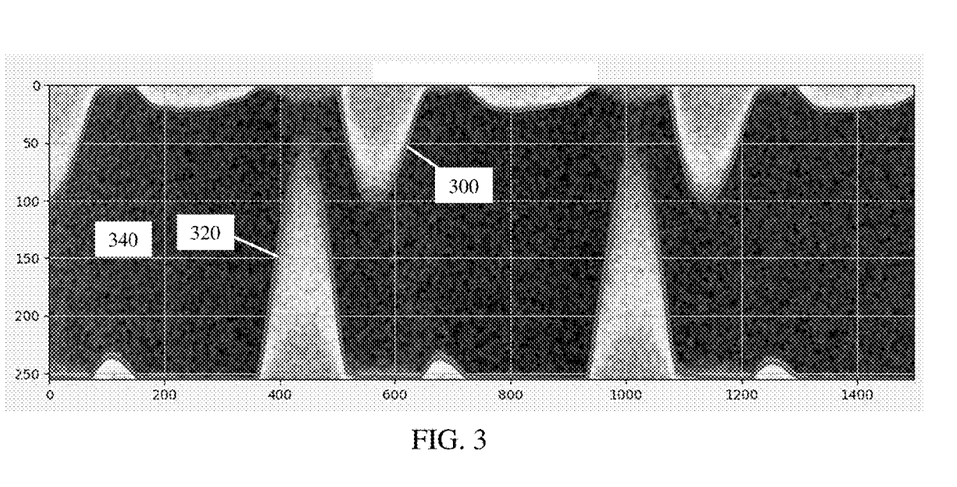
FIG. 3 illustrates an example plotting of spectra from 0 to $2\pi$.

FIG. 3 shows an example. In FIG. 3, "0" on the y-axis is $2\pi$, and "256" on the y-axis is 0. The black or dark regions represent noise while the whiter or gray regions represent signal.

By plotting each spectrum to begin at 0 and end at $2\pi$, the negative signal is in the upper region (i.e., along or extending from $2\pi$ towards 0) and the positive signal is in the lower region (i.e., along or extending from 0 towards $2\pi$). In alternative embodiments, the plotting is from $2\pi$ to 0 so that the positive is in the upper region and the negative is in the lower region. Either of 0 to $2\pi$ or $2\pi$ to 0 is plotting over time from 0 to $2\pi$.

In a typical spectral strip, this plotting would not be used. The spectral strip is to show the positive signal in the top half and the negative signal in the bottom half, where other separations than half may be used due to baseline shift to avoid aliasing. Unlike this typical, the plotting of act 220 is to better separate the positive and the negative with noise in-between. This plotting from 0 to $2\pi$ or $2\pi$ to 0 places the noise region 340 in between the signals and avoids aliasing.

The plotting from substantially 0 to $2\pi$ or $2\pi$ to 0 assists in band separation without aliasing. In an alternative embodiment, the velocity scale is plotted with the baseline at any position. A machine-learned model or signal processing is applied to distinguish the bands to set the boundary no matter how plotted. The boundary separates the bands so varies over time or spectrum-by-spectrum.

In act 230 of FIG. 2, the signal processor detects positive and/or negative spectral envelopes over time based on the spectra as plotted from 0 to $2\pi$. The edge of the signal with the noise is detected. In the example of FIG. 3, there are two bands (positive and negative). The edge of each band is separately detected. Where only one band is represented in the spectra or spectrum, then the envelope is detected for that one band (e.g., only positive or only negative). More than two bands may be detected.

Act 232 represents one approach for separate detection of the spectral envelopes or bands. Each spectrum is divided into band regions bounded by a limit in the noise region 340. In other embodiments, thresholding based on noise is used so that the spectrum is divided into bands without noise.

In act 232, the signal processor identifies, for each spectrum of the spectra, a point in a noise region between one signal and another signal, 0, or $2\pi$. The points across the spectra (over time) define a boundary over time. The boundary is formed by the points of the spectra. Since the points are positioned spectrum-by-spectrum, the boundary formed by the points of the spectra varies relative to 0 and $2\pi$.

To identify each point for the boundary, the signal processor searches each spectrum. The signal processor searches for one or more bands, such as a band of positive signals and a band of negative signals. To search for the edges of the band, a noise level is determined to distinguish noise from signal. The amplitude of the energy modulation is used to define the noise level. A statistical analysis finds the noise floor. For example, the energies are sorted by magnitude. A transition in magnitude is determined from the sorted energies, such as by slope. Strong versus weak signals are identified to set a noise level or threshold distinguishing signal from noise.

The edge is then found that separates strong signal from noise signal (i.e., the threshold noise level). A number of energies above the noise in a row may be used to find the edge. The edge divides into separate regions. In an alternative approach, the energies for a group of or all spectra are low pass filtered, removing outliers. The threshold is then applied to identify the signal regions or the noise region 340. Other approaches using the noise level to search for the signals or different bands may be used.

Figure 4:
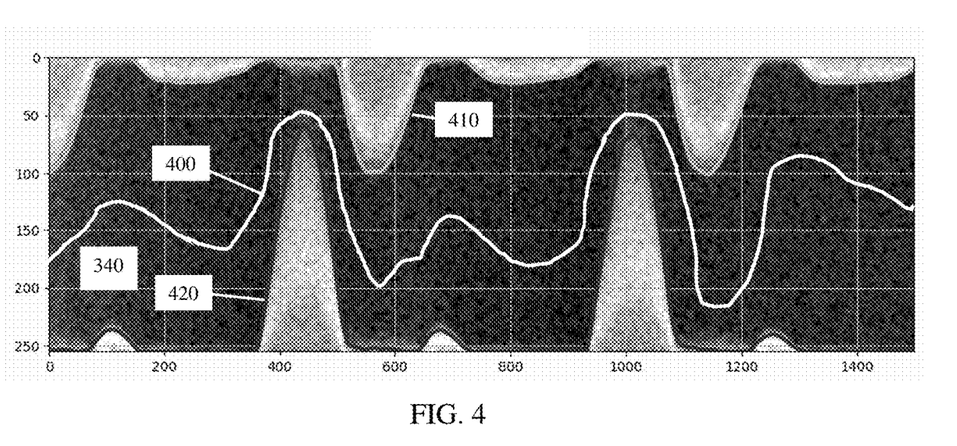
FIG. 4 illustrates an example dynamic boundary or search limit identified for the plot of FIG. 3.

Once the edges are located for a spectrum, the point is positioned in the noise region 340 between the signals, bands, or edges. FIG. 4 shows an example. The spectral edges of the positive and negative signals 420, 410 are used to set the points spectrum-by-spectrum, forming the boundary 400 in the noise region 340. In this example, each point and the resulting boundary 400 is placed halfway between the edges or envelopes of the two bands. For example, the point at time 400 is about 57 based on the edge 410 of the negative signal being at 10 and the edge 420 of the positive signal being 125. As another example, the point at time 1 is 178 based on the edge 410 of the negative signal being at 100 and the edge of the positive signal being at 256. Other divisions than half may be used. More than one boundary may be used, such as setting points based on each band a certain range away or by % (e.g., ⅓ of noise band from edge 410 and ⅓ of noise band from edge 420 where ⅓ is of the noise between).

Where the positive or negative signal is not present for a given spectrum, 0 or 2π is used as the envelope or edge 410, 420. In the example of FIG. 4, 0 is used for the positive edge 420 from about times 0-75, 125-375, 525-630, 700-950, 1075-1225, and 1275-1500, and 2π is used for the negative edge 410 from 75-125, 700-725, 950-1050, and 1225-1275. For each spectrum, the point is positioned in the noise region 340 between the positive or negative signal and (1) the other of negative or positive signal when the other signal is found in the searching or (2) 0 or 2π when the other signal is not found.

The boundary 400 is a limit used in searching for tracing. Rather than using the baseline set to separate bands, the search for the spectral envelope uses a limit or velocity defined by the boundary 400. The boundary 400 acts as a dynamic or variable Nyquist limit with different values (points) for different times, avoiding aliasing.

In act 240 of FIG. 2, the signal processor traces the spectral envelope over time. The same approach to detect the spectral envelope in act 230 or otherwise find the edge of a band or signal may be used. Different approaches may be used. For example, a more processing efficient but less precise band edge or signal-noise boundary detection is performed in act 230 to find the boundary in act 232, and a more processing intensive and precise band edge or signal-noise boundary detection is performed in act 240 to trace. As another example, the detection of act 230 is performed without limits other than 0 and 2π, and the tracing of act 240 limits where the search for the edge occurs. Any now known or later developed spectral envelope tracing may be used.

In another embodiment, a peak velocity search is performed. The tracing is performed for all or only a part of the time (one or small number of spectra). The tracing may be less than for all spectra.

The tracing locates the edge of the signal over time or at a time. For example, the maximum positive and/or maximum negative signal over one or more heart cycles is determined. A noise threshold is found from the spectra and used as a threshold to identify signal. The trace is placed where signal is mostly on one side of the trace and noise is mostly on the other side of the trace. The trace locates the edge of the signal over the spectra. The maximum of this trace is then found.

The tracing of act 240 is limited by the points forming the band separation. Rather than relying on the baseline positioning to define where positive and negative are separated, the dynamic or variable boundary identified in act 232 is used. Since this boundary changes by spectrum, only positive signal is provided in the positive signal side of the boundary, and only negative signal is provided in the negative signal side of the boundary. The searching for the positive spectral envelope is on one side of the boundary, and the searching for the negative spectral envelope is on another side of the boundary. Aliasing is avoided.

The signal processor locates the edge of each band (e.g., positive signal and negative signal) with the noise region or noise regions. The edge extends over time or spectra. The located edges are the spectral envelope. Using FIG. 4 as an example of tracing rather than identifying the boundary 400, the traces 410 and 420 are located as the spectral edges. The spectrum may be re-plotted, such as based on a baseline position (e.g., baseline 0 so replotted from −π to π). The boundary 400 is used to limit the tracing so that even with the re-plotting aliasing is avoided. Any aliased signal is not included in the wrong signal as the boundary 400 indicates the actual band membership. The positive signal is traced as between 0 to the points or boundary 400, and the negative signal is traced as between 2π and the points or boundary 400, resulting in the spectral envelope without aliasing regardless of the baseline position.

In act 250 of FIG. 2, the signal processor generates an image on a display. The image is of the spectral envelope or is of information that is a function of the spectral envelope.

In one embodiment, a spectral strip or spectral Doppler image is generated for the Doppler gate. Filtering may be applied to smooth the spectra along the time and/or frequency dimensions or over energy. The spectral strip shows the frequency modulated by energy as a function of time. Any now known or later developed spectral strip mapping may be used, such as gray scale mapping with the intensity representing energy. The energies modulate the pixels. The gray scale or color is mapped from the energy values.

The traced spectral envelope is also displayed. The spectral envelope as traced is included in the image, such as being highlighted by coloring or an overlaid graphic (e.g., a curve or line along the edge). Different colors may be used for different bands. Additional information may be included, such as an annotation with alphanumeric text showing a maximum for one or more of the bands (e.g., maximum positive velocity).

The velocity scale defines a vertical range on the spectral strip. The baseline defines a separation of positive and negative within the velocity scale. The spectral envelope is displayed with positive above the baseline and negative below the baseline. As additional samples are acquired, the resulting spectra for different times are added to the spectral strip, such as adding the spectra to a right side of the strip, shifting the remaining spectra one temporal step to the left, and removing the leftmost spectral strip. Another update or scrolling of the spectral strip may be used.

The spectral strip may or may not be displayed with a spatial image, such as a one-dimensional M-mode, two-dimensional B-mode, two-dimensional F-mode (flow mode), or combination thereof image. The location of the gate may be indicated graphically in the image, such as represented by a circle, double line, or other graphic in the field of view.

In an additional, or alternative, embodiment, information derived from the spectral envelope is displayed in an image. For example, the spectral envelope is used to detect a maximum positive and/or negative velocity. The maximum(s) are displayed in any image as alphanumeric text or represented graphically (e.g., maximum for the patient referenced to a disease grading and/or population chart). As another example, the maximum and/or other statistical information (e.g., standard deviation) of the energy and/or velocity is determined and displayed. In yet another example, statistical information from the spectral envelope is used for disease grading or another diagnostic or prognostic rating, such as the strandness criterion. The grading, diagnostic, or prognostic results are displayed.

FIG. 5 shows a system 500 for spectral Doppler imaging. The system 500 uses a dynamically determined boundary, such as a boundary based on mapping or plotting spectra from substantially 0 to $2\pi$, to trace the spectral envelope. Aliasing may be avoided using the dynamically determined boundary and/or substantially 0 to $2\pi$ plotting.

The system 500 is a medical diagnostic ultrasound imaging system. Other imaging systems may be used, such as a workstation loading samples from memory or other source.

The system 500 includes a transmit beamformer 510, a transducer 520, a receive beamformer 530, a Doppler processor 540, a display 550, a signal processor 560, and a memory 570. Additional, different or fewer components may be provided, such as the system 500 without the front-end beamformers 510, 530 and/or transducer 520 or the system 500 with a scan converter. The Doppler processor 540 and signal processor 560 may be combined into one device acting as both processors, or additional processors for sequential or parallel processing may be used. A user input may be provided for placing the gate and/or sizing the gate.

The system 500 implements the method of FIG. 1. The beamformers 510, 530 and transducer 520 are used to acquire the samples. The Doppler processor 540 estimates the spectra for the gate from the samples. The Doppler processor 540 and/or signal processor 560 plot from substantially 0 to $2\pi$ and/or determine the boundary between bands, trace, and cause display of the traced spectral envelope or information derived therefrom. Other methods may be implemented. The Doppler processing may be performed either before or after CINE.

The transducer 520 is an array of a plurality of elements. The transmit beamformer 510 is shown separate from the receive beamformer 530. Alternatively, the transmit and receive beamformers 510, 530 may be provided with some components in common. Operating together or alone, the transmit and receive beamformers 510, 530 form beams 524 of acoustic energy for sampling a range gate 522 and/or scanning a one, two, or three-dimensional region.

The transmit beamformer 510 is configured to transmit a sequence of transmit beams 524 of ultrasound energy. The acoustic energy is directed at the Doppler gate 522, but may be focused elsewhere (e.g., the Doppler gate is along the scan line but not at the focus). The beam 524 of acoustic energy is transmitted to the Doppler gate 522 or to other locations.

An ongoing sequence of transmit beams 524 are generated at a PRF. The PRF determines the interval between temporally adjacent transmissions or transmit beams 524. The PRF may be low enough to have a period of no transmission not needed for travel time, interleaving with other imaging modes, and reverberation reduction. In one embodiment, the PRF is established based on the velocity scale, the travel time, interleaving, and reverberation reduction. In other embodiments, the PRF is set based on the velocity scale and the Nyquist criterion.

The receive beamformer 530 forms one or more receive beams 526 in response to each transmit beam 524. While shown in parallel, the receive beams 526 may be colinear or at an angle to the transmit beams 524. Acoustic echoes are received by the transducer 520 in response to the transmitted acoustic energy. The echoes are converted into electrical signals by the transducer 520, and the receive beamformer 530 forms the receive beams 526 from the electrical signals to generate samples representing the location or locations within the range gate 522.

Given the ongoing transmit beams 524 at the PRF or PRI (pulse repetition interval) for each location, samples are generated in an ongoing manner as well. Responses over time are acquired. The responses create ensembles or accumulations of samples used to estimate spectra representing the same period.

The Doppler processor 540 is a spectral Doppler estimator. Other imaging detectors may be included, such as a B-mode detector. In one embodiment, the Doppler processor 540 is a digital signal processor or other device for applying a transform to the receive beam sample data. A sequence of transmit and receive events is performed over a period. A buffer (e.g., corner turning memory) or the memory 570 stores the receive beamformed data from each transmit and receive event. A wall filter, such as a programmable filter for distinguishing between tissue and fluid motion, may filter the samples prior to application of the transform. Any number of transmit and receive events may be used for determining a spectrum, such as three or more. The Doppler processor 540 estimates the spectra for the gate. By applying a discrete or fast Fourier transform or other transform to the ultrasound samples for the same gate, the spectra representing the responses from the gate are determined. Histograms or data representing the energy level at different frequencies for the period to acquire the samples are obtained. Velocity may be determined from the frequency or frequency is used without conversion to velocity.

By repeating the process, the Doppler processor 540 may obtain different spectra for a given gate at different times. Overlapping data may be used, such as calculating each spectrum with a moving window of selected ultrasound samples. Alternatively, each ultrasound sample is used for a single period and corresponding spectrum.

The Doppler processor 540 applies the transform for a range of frequencies. The range of frequencies or velocity scale limits the positive and negative velocities resulting from the estimation. Any of various velocity scales may be used, up to and including a velocity scale equal to the transmission PRF. The spectra are estimated using a given velocity scale. Similarly, the baseline or center of the velocity scale may be set.

The signal processor 560 may be part of the Doppler processor 540 or a separate processor. The signal processor 560 is a general processor, control processor, digital signal processor, application specific integrated circuit, field programmable gate array, graphics processing unit, analog circuit, digital circuit, combinations thereof, or another now known or later developed device for processing. The signal processor 560 is configured by software, firmware, and/or hardware.

The signal processor 560 is configured to identify a line in a noise region between two bands or one of the bands and 0 and $2\pi$. Other lines may be identified between other bands or the velocity scale limits. The line may be determined between other plottings, such as from $-\pi$ to $\pi$.

The signal processor 560 identifies the line as a curve (i.e., the line varies over time within the velocity scale). The line is continuous but may be discontinuous. A line fitting may be performed. Filtering of the points may be used. The line varies over time spectrum-by-spectrum of the spectra but may vary by groups of spectra. To avoid aliasing, the line is positioned in the noise between bands and/or a band and the velocity scale limit (e.g., 0 or $2\pi$). The line is positioned halfway between the two bands (between band edges) or band and the limit of the velocity scale (e.g., 0 or $2\pi$). Other positions, such as spacing closer to one band than the other, may be used.

The signal processor 560 may plot the spectra from 0 to $2\pi$ such that one of the two bands is by $2\pi$ and the other of the two bands is by 0. This may assist in identifying the line separating the bands. The spectra as plotted are used to position the line in a noise region.

The signal processor 560 is configured to limit a search for a spectral envelope of the spectra by the line. The line defines or separates the different bands. Rather than tracing based on the baseline position for a given velocity scale, the dynamic line is used to define the search region. Instead of searching for one band above the baseline and another band below the baseline, the identified line or boundary is used to limit the search for each band. As a result, the search or tracing does not include aliasing.

The display 18 is a CRT, monitor, LCD, plasma screen, projector, printer, or another now known or later developed display for displaying an image of the spectral envelope or information derived from the spectral envelope. For a spectral Doppler image, a range of velocities with each velocity modulated as a function of energy is provided as a function of time.

The spectral envelope is displayed on the spectral Doppler images as a trace or graphic. The peak velocity or other information derived from the spectral envelope may be displayed on the spectral Doppler image (e.g., annotation) or as a separate image.

Other image configurations may be provided, including colorized spectral Doppler images. A color or flow mode image may be generated, such as showing mean velocity as a function of location in a region of interest in a grayscale B-mode.

The memory 570 stores ultrasound samples, estimated spectra, settings, image data, spectral plots, dividing line or points forming a dynamic line, signal edges, traces, annotations, and/or other information. The memory 570 may store information from any stage of processing or used for generating a display.

In one embodiment, the memory 570 is a non-transitory computer readable storage medium having stored therein data representing instructions executable by the programmed Doppler processor 540 and/or signal processor 560 for Doppler imaging. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts, or tasks illustrated in the figures or described herein are executed in response to one or more sets of instructions stored in or on computer readable storage media. The functions, acts, or tasks are independent of the particular type of instructions set, storage media, processor, or processing strategy and may be performed by software, hardware, integrated circuits, firmware, micro code or the like, operating alone or in combination. Likewise, processing strategies may include multiprocessing, multitasking, parallel processing and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for spectral Doppler imaging, the method comprising:
   acquiring, with an ultrasound system, samples representing response from a range gate;
   estimating, by a Doppler estimator, spectra over time for the range gate from the samples;
   plotting the spectra over time from 0 to $2\pi$;
   identifying, for each spectrum of the spectra, a point in a noise region between a first signal and a second signal, 0, or $2\pi$;
   tracing a spectral envelope over time, the tracing limited by the points for the spectra; and
   displaying the spectral envelope or information derived from the spectral envelope in an image.

2. The method of claim 1 wherein acquiring comprises transmitting with a pulse repetition frequency and acquiring one of the samples in response to each repetition.

3. The method of claim 1 wherein estimating comprises applying a Fourier transform to the samples, each spectrum of the spectra comprising energy as a function of frequency for a period.

4. The method of claim 1 wherein plotting comprises plotting each spectrum to begin at 0 and end at $2\pi$ such that negative signal extends from $2\pi$ towards 0 and positive signal extends from 0 towards $2\pi$.

5. The method of claim 1 wherein identifying comprises positioning the point halfway between the first signal and the second signal, 0, or $2\pi$.

6. The method of claim 1 wherein identifying comprises searching for a band with the first signal and a band with the second signal in the spectrum, and positioning the point in the noise region between the first signal and (1) the second signal when the second signal is found in the searching or (2) 0 or $2\pi$ when the second signal is not found.

7. The method of claim 1 wherein identifying comprises determining a noise level from at least some of the spectra and using the noise level to search for the first and second signals.

8. The method of claim 1 wherein identifying comprises positioning a boundary over time, the boundary formed by the points of the spectra and varying relative to 0 and $2\pi$.

9. The method of claim 1 wherein tracing comprises locating an edge of the first signal with the noise region and locating an edge of the second signal with the noise region, the locating of the edges being over time, and the edges comprising the spectral envelope.

10. The method of claim 1 wherein tracing comprises using 0 or 2π for the spectra where the noise region extends to 0 or 2π and the first or second signal where the noise region does not extend to 0 or 2π.

11. The method of claim 1 wherein tracing comprises tracing the first signal as a positive signal as between 0 to the points for the spectra and tracing the second signal as a negative signal as between 2π and the points for the spectra.

12. The method of claim 1 wherein displaying comprises displaying the spectral envelope with positive above a baseline and negative below a baseline.

13. The method of claim 1 wherein displaying comprises displaying the information, the information being based on a peak velocity of the spectral envelope.

14. A method for spectral Doppler imaging, the method comprising:
   acquiring, with an ultrasound system, samples representing response from a range gate;
   estimating, by a Doppler estimator, spectra over time for the range gate from the samples;
   plotting the spectra over time from 0 to 2π;
   detecting positive and/or negative spectral envelope over time based on the spectra as plotted from 0 to 2π; and
   displaying the spectral envelope or information derived from the spectral envelope in an image.

15. The method of claim 14 wherein plotting comprises plotting each spectrum to begin at 0 and end at 2π such that negative signal extends from 2π towards 0 and positive signal extends from 0 towards 2π.

16. The method of claim 14 wherein detecting comprises setting a boundary that varies along the 0 to 2π spectrum by spectrum, and searching for the positive spectral envelope on one side of the boundary and searching for the negative spectral envelope on another side of the boundary.

17. The method of claim 16 wherein setting the boundary comprises setting the boundary halfway between signals of different bands where 0 or 2π is used instead of the signal for spectrum without signal in the band.

18. A system for spectral Doppler imaging, the system comprising:
   a beamformer configured to sample a gate at a pulse repetition interval established in response to a velocity scale;
   a Doppler estimator configured to generate multiple spectra from the sampling of the gate;
   a signal processor configured to identify a line in a noise region between two bands or one of the bands and 0 and 2π, the line varying over time spectrum-by-spectrum of the spectra and limit a search for a spectral envelope of the spectra by the line; and
   a display configured to display the spectral envelope or information derived from the spectral envelope.

19. The system of claim 18 wherein the signal processor is configured to plot the spectra from 0 to 2π such that one of the two bands is by 2π and the other of the two bands is by 0, and identify the line from the spectra as plotted in a noise region.

20. The system of claim 18 wherein the signal processor is configured to position the line spectrum-by-spectrum halfway between the two bands.

* * * * *